United States Patent
Ralfs

(10) Patent No.: US 8,485,981 B2
(45) Date of Patent: Jul. 16, 2013

(54) MEDICAL THERAPY DEVICE

(75) Inventor: Frank Ralfs, Luebeck (DE)

(73) Assignee: Draeger Medical Systems, Inc., Telford, PA (US)

( * ) Notice: Subject to any disclaimer, the term of this patent is extended or adjusted under 35 U.S.C. 154(b) by 1025 days.

(21) Appl. No.: 12/145,886

(22) Filed: Jun. 25, 2008

(65) Prior Publication Data
US 2009/0326389 A1    Dec. 31, 2009

(51) Int. Cl.
*A61B 5/02*    (2006.01)
*F16K 31/02*    (2006.01)

(52) U.S. Cl.
USPC ..................... 600/485; 128/204.21

(58) Field of Classification Search
None
See application file for complete search history.

(56) References Cited

U.S. PATENT DOCUMENTS

| | | | |
|---|---|---|---|
| 4,745,920 A | 5/1988 | Forssmann et al. | |
| 7,177,386 B2 | 2/2007 | Mostafavi et al. | |
| 7,509,157 B2 | 3/2009 | Hayek | |
| 2005/0056283 A1 | 3/2005 | Levi | |
| 2005/0065567 A1* | 3/2005 | Lee et al. | 607/17 |
| 2007/0149860 A1* | 6/2007 | Lynn et al. | 600/300 |

OTHER PUBLICATIONS

Berryhill et al., "PEEP-induced Discrepancy Between Pulmonary Arterial Wedge Pressure and Left Atrial Pressure: The Effects of Controlled vs. Spontaneous Ventilation and Compliant vs. Noncompliant Lungs in the Dog," Anesthesiology, 51:303-308, (1979).
Berryhill et al., "Pulmonary Vascular Pressure Reading at the End of Exhalation," Anesthesiology, 49(5):365-368, (1978).
Keckeisen, Maureen, "Monitoring Pulmonary Artery Pressure," Critical Care Nurse, 24(3):67-70, (2004).
Nadeau et al., "Misinterpretation of pressure measurements from the pulmonary artery catheter," Can Anaesth Soc J., 33(3):352-363, (1986).
Oden et al., "Detection of End-exhalation Period by Airway Thermistor: An Approach to Automated Pulmonary Artery Pressure Measurement," Anesthesiology, 58:467-471, (1983).

* cited by examiner

*Primary Examiner* — Jim Ketter
*Assistant Examiner* — Reza Ghafoorian
(74) *Attorney, Agent, or Firm* — Mintz Levin Cohn Ferris Glovsky and Popeo, P.C.

(57) ABSTRACT

A system and a method for synchronizing operation between a patient monitoring device and a patient treatment device are disclosed. The patient monitoring device and the patient treatment device are operatively connected via a network, for example, a patient area network (PAN) or a local area network (LAN). A controller with a display is configured to accept user input via a graphic user interface (GUI) and display a patient's physiological data and operating parameters of both the patient monitoring device and the patient treatment device. The operation is synchronized by starting to operate the patient monitoring device at a predetermined operating state of the patient treatment device, and delaying changes in the operating state of the patient treatment device, until the operation of the monitoring device is concluded or the operating state of the patient treatment device indicates an abort condition.

12 Claims, 3 Drawing Sheets

MEDICAL THERAPY DEVICE

FIELD OF THE INVENTION

The present invention relates to a healthcare monitoring and treatment system, and more particularly to cooperation between a ventilator and/or anesthesia device and a patient monitoring and/or imaging device.

BACKGROUND OF THE INVENTION

Hospitals routinely monitor physiological parameters of patients from first entry until final release using one or more patient monitoring devices, such as a heart rate monitor, an EKG monitor, a $SpO_2$ monitor, and so forth. These devices detect physiological parameters and tend to operate independently of each other. The monitoring equipment includes connections to the patient necessary to measure the physiological parameter and a display device for displaying the physiological parameter. A clinician, e.g., a nurse, reads the information on the various display devices and records the patient's vital signs.

Current systems have integrated the measurement of some of the physiological parameters (e.g. EKG, $SpO_2$, etc.) into a single patient monitoring device. Such a device includes the patient connections necessary to measure the physiological parameters measurable by the device and a display device which can display the measured physiological parameters in an appropriate manner. Such patient monitors may be considered to be partitioned into two sections. A first, operational, section controls the reception of signals from electrodes connected to the patient and performs the signal processing necessary to calculate the desired physiological parameters. A second, control, status and communication section interacts with a user to receive control information and with the operational section to receive the physiological parameters, and displays status information and the values of the physiological parameters in an appropriate manner. Either or both of these sections may include a computer or processor to control the operation of that section. This approach has an economic advantage since the control, status and communication section is shared among the parameter monitoring functions.

Such patient monitoring devices may also be connected to a central hospital computer system via a hospital network. In this manner, data representing patient physiological parameters may be transferred to the central hospital computer system for temporary or permanent storage in a storage device. The stored data may be retrieved and analyzed by healthcare workers via the hospital network. Patient monitoring devices in such networked system include a terminal connected to and communicating with the hospital network. The control, status and communication section controls the display of the physiological parameters, and also the connection to the hospital network and the exchange of the physiological parameters with other systems, such as other patient monitoring devices and/or the central computer storage device, via the hospital network.

Such patient monitoring modules may also be portable or transportable. That is, they may operate while being transported with a patient who is being moved from one location to another in the hospital, for example, between a patient room and a therapy or operating room. A portable patient monitor consists of a base unit, and a portable unit which may be docked and undocked from the base unit. Base units may be placed at appropriate locations in the hospital. They are permanently connected to the hospital network and receive power from the power mains. The portable unit includes the necessary patient connections, connections for docking with base units, and a display screen. The portable unit also includes a processor which controls the operation of the portable unit. The portable unit further includes a battery and an internal memory device.

Throughout the specification, the terminology "module" and "device" will be used interchangeably.

A patient monitor is passive in the sense that it monitors physiological parameters of the patient to which it is attached. However, other medical devices are active devices, herein sometimes also referred to as treatment devices, in that their operation affects the patient in some manner. For example, the anesthesia module controls the administration of anesthesia to a patient, e.g. during an operation; the fluid management device controls the administration of fluids (blood, saline, and/or medication) to a patient; the ventilator device assists or controls breathing of a patient, e.g. during an operation, and so forth. The active devices also include a computer or processor which controls the operation of the device. These devices also may be connected to a hospital network through a base unit. This allows a central location to monitor and to control the active device. As with the patient monitoring device, an active device, such as a fluid monitoring device, may be portable in the sense that a control module, including a processor, may be undocked from a fixed unit. This control module continues to operate the device, at the last received control settings, e.g. while a patient is transported from one location to another. When at the new location, the control module may be docked in a fixed unit at the new location and control by a central computer resumed.

Patient monitors have also been adapted to transmit information to the hospital network from other modules. These modules may be patient monitoring modules measuring physiological parameters which are not measured by the patient monitor, or patient treatment modules reporting the status of treatments being provided to the patient. Such patient monitors include input terminals, which may be wireless input ports, to which these other monitoring modules can be connected. Information from these modules can be passed through the patient monitor to the hospital network through the base unit.

Independently operating systems used in patient monitoring and treatment have numerous limitations. For example, altering a treatment protocol based on monitoring results may require intervention by a clinician reading parameters from the monitoring device and changing operating parameters in the treatment device based on the read parameters. Likewise, monitoring functions may have to be altered based on an operational state of a treatment device. There is a significant risk of a mistake being made in the settings of one device based on the readings from another.

A system which addresses these deficiencies and associated problems is desirable.

BRIEF SUMMARY OF THE INVENTION

In accordance with principles of the present invention, a method and a system are disclosed for synchronizing operation between a patient monitoring device and a patient treatment device. The system includes a controller operatively connected to the patient monitoring device and the patient treatment device, wherein the controller is configured to detect an initial status of the patient treatment device; start a requested procedure with the patient monitoring device in response to the initial status; continuously monitor an operating status of the patient treatment device while the requested procedure is performed; and terminate the procedure, if the operating status of the patient treatment device indicates an abort condition.

In one embodiment, the patient treatment device may be a ventilator, wherein the initial status of the ventilator indicates completion of an inspiration stroke or an expiration stroke. For a ventilator, the abort condition may indicate that a lower threshold for $SpO_2$ is violated, that a presettable apnoeic time $T_{apn}$ has been reached, or that a lower limit value for a minute volume has been reached.

According to one embodiment of the invention, an impending event of the patient treatment device is detected while monitoring the operating status and the event is delayed until the procedure is complete, or until the operating status of the patient treatment device indicates an abort condition. For a ventilator, the impending event is an expiration, if the initial status indicated completion of an inspiration stroke, or an inspiration, if the initial status indicated completion of an expiration stroke.

According to another embodiment of the invention, the patient monitoring device may be an imaging device, which acquires an image, or a device that measures intrathoracic blood pressure, such as pulmonary arterial pressure (PAP) or a pulmonary capillary wedge pressure (PCWP), while the patient treatment device is in a predefined operating state. This increases the accuracy of the measurement.

According to yet another embodiment of the invention, the system may include an operator console with a display device, with the display device configured to display physiological patient data and parameter settings from the patient monitoring device and the patient treatment device and receiving user input via a graphic user interface (GUI). Preferably, the patient data, parameter settings and other measurement data are integrated for display.

Further features and advantages of the present invention will be apparent from the following description of preferred embodiments and from the claims.

BRIEF DESCRIPTION OF THE DRAWINGS

The following Figures depict certain illustrative embodiments of the invention in which like reference numerals refer to like elements. These depicted embodiments are to be understood as illustrative of the invention and not as limiting in any way.

DETAILED DESCRIPTION OF THE INVENTION

Figure 1:
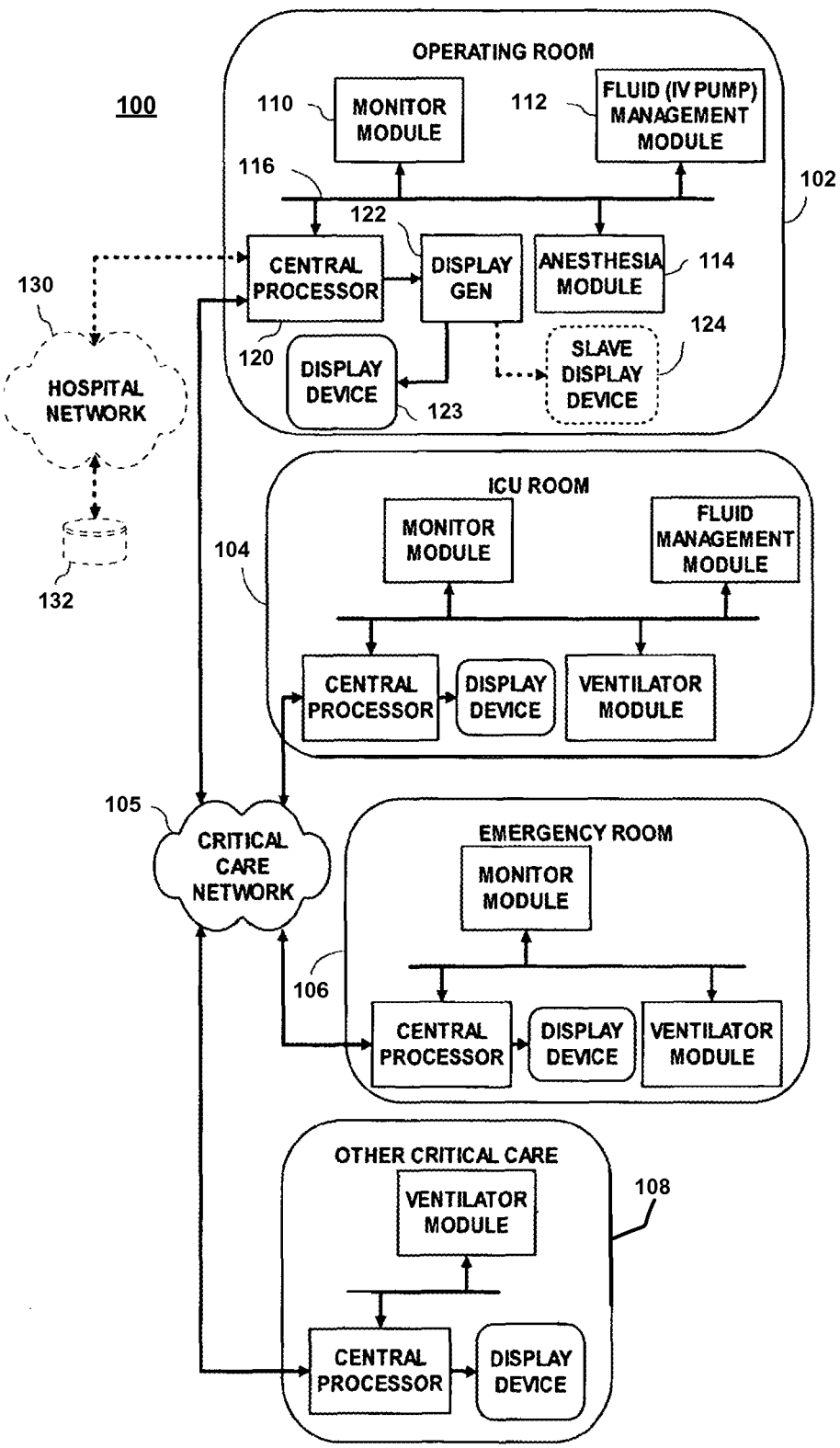
FIG. 1 is a block diagram of a hospital system for monitoring patients and providing treatment to patients according to principles of the present invention.

FIG. 1 is a block diagram of an exemplary hospital system 100 for monitoring and providing treatment to patients. The exemplary hospital system 100 includes an operating room 102, an ICU room 104, an emergency room 106, and a room 108 providing other critical care. The overall number of hospital rooms 102, 104, 106, 108 is exemplary only and not limiting in any way. The various rooms may have similar or different equipment, as described below.

For example, the operating room 102 includes a patient monitoring module 110 for acquiring and processing signals derived from sensors (not shown) suitable for attachment to a patient. The operating room 102 also includes exemplary patient treatment modules: a fluid infusion (IV pump) control and management module 112 and an anesthesia module 114. The modules 110, 112 and 114 are coupled to a central processor 120 via a patient area network (PAN) 116. The exemplary ICU room 104 includes a monitor module, a fluid management patient treatment module and a ventilator module, also coupled to a central processor via its own PAN. The emergency room 106 includes a monitor module and a ventilator patient treatment module coupled to a central processor via its own PAN. The other critical care room 108 includes a ventilator patient treatment module, likewise coupled to the central computer via its own PAN.

In operation, the PAN 116 may be implemented in any manner allowing a plurality of modules within a treatment room to intercommunicate. For example, the PAN 116 may be implemented as an Ethernet network, either wired or wireless (WLAN). If implemented as a wireless network, it may be implemented according to available standards, such as: (a) a WLAN 802.11b compatible standard, (b) 802.11a compatible standard, (c) 802.11g compatible standard, (d) Bluetooth 802.15 compatible standard, and/or (e) GSM/GPRS compatible standard communication network.

Figure 2:
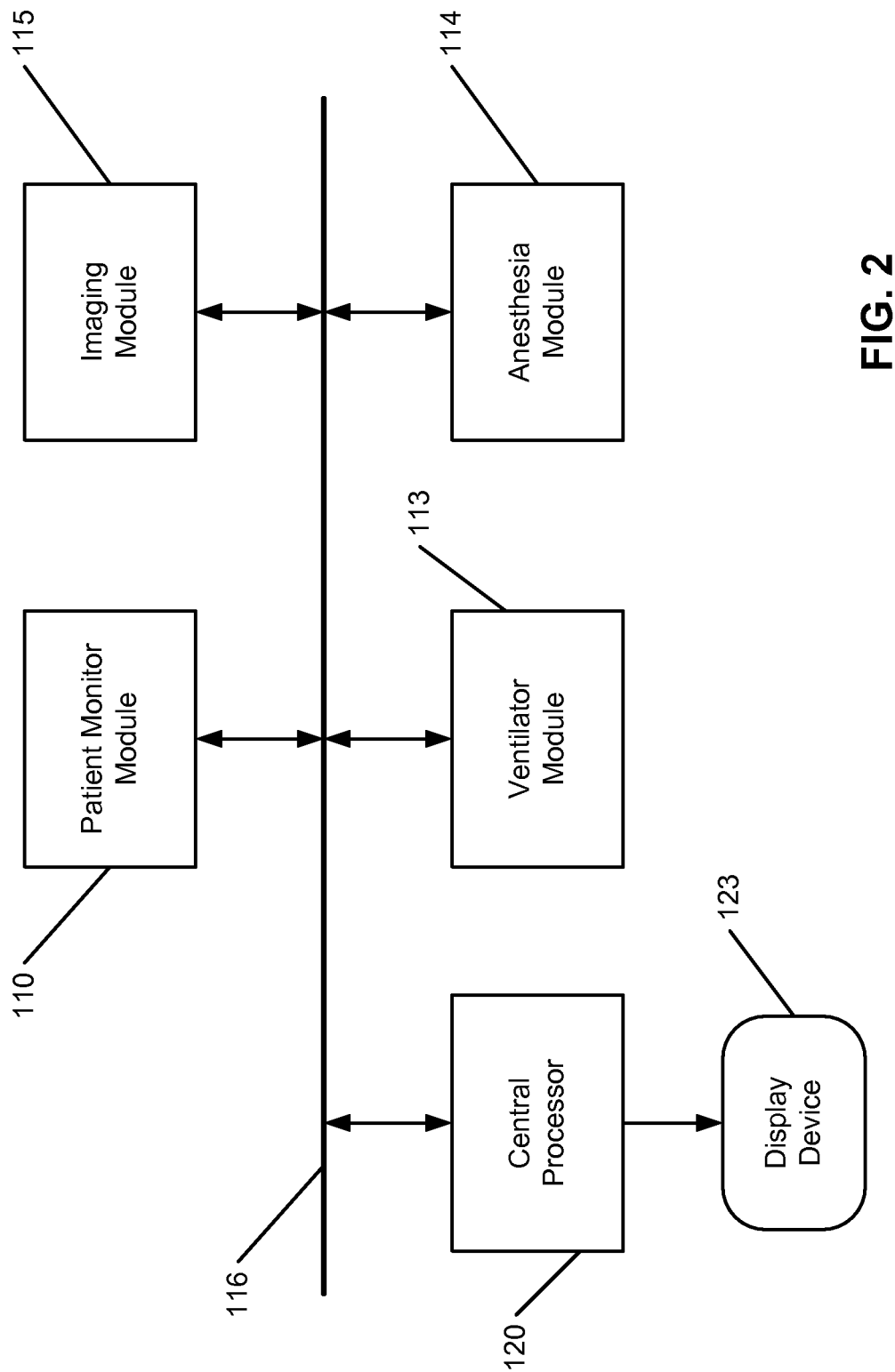
FIG. 2 is a more detailed block diagram illustrating interconnected patient monitoring/imaging modules and patient treatment modules.

The term "module" in the context of the present invention, as illustrated in FIGS. 1 and 2, refers not only to the control portion of a patient monitoring or treatment apparatus, but is meant to encompass the entire system, including sensors, cabling, pumps, motors and the like, which may be required to measure and/or control the physiological patient parameters.

The PAN's 116 in the various rooms 102, 104, 106, 108 are each coupled to a central processor 120 for data exchange. The central processor 120 may be coupled to a display generator 122 which supplies to display devices 123 data, preferably in integrated form, from at least some of the various patient monitor and treatment modules 110, 112, 114 placed throughout the hospital. The display generator 122 may also be coupled to an additional slave display device 124, as illustrated in phantom. Although a central processor 120 is indicated in FIG. 1 as being located in each of the rooms 102, 104, 106, 108, it will be understood that this need not be the case and that a single centrally placed central processor may manage the critical care network, with connections between the central processor and the various PANs 116 provided via a LAN or another suitable network connection.

The patient monitoring module 110 connected to PAN 116 processes the signals representing the physiological patient parameters and provides that information to the central processor 120. These parameters may be relatively standard physiological parameters, such as EKG, heart rate, SpO2, etc. The central processor 120 may also initiate generation of a new parameter based on signals derived using the patient monitoring module 110 and/or the patient treatment modules 112, 114. For example, the new parameter may be associated with (a) gas exchange, (b) skin color, (c) hemodynamics, (d) pain and/or (e) electro-physiology. Similarly, the patient treatment modules, i.e. the fluid management module 112 and the anesthesia module 114, receive operational data from the central processor 120 via the PAN 116 and in response perform their treatment functions, e.g. monitoring fluids administered to the patient and supplying anesthesia to the patient, respectively. Concurrently, the patient treatment modules 112, 114 send status data to the central processor 120 via the PAN 116.

The central processor 120 may also interact with a user, for example, by way of a graphic user interface (GUI) on display device 123, 124, to receive patient identifier information and treatment instructions and parameters. The central processor 120 configures the patient treatment modules 112, 114 by sending the patient identifier information, the treatment instructions and parameters to the patient treatment modules 112 and 114 via the PAN 116.

The patient monitoring and/or treatment modules 110, 112, 114 may include a dedicated processor (not illustrated) for receiving the configuration parameters from the central processor 120, for controlling the operation of the module 110, 112, 114 and for sending status and patient physiological parameter information to the central processor 120 via the PAN 116. The configuration parameters may include patient identifier information, set-up parameters, and/or data representing executable instructions for execution by the processor in the module 110, 112, 114 in processing data to be provided to the central processor 120. The modules 110, 112, 114, in turn, use the received configuration parameters, and executable instructions in supporting their operation, e.g. for processing data to be provided to the central processor 120.

The central processor 120 conditions the display generator 122 to generate signals representing an image for displaying these physiological parameters in an appropriate manner, e.g. a waveform, a status phrase or a number. The image generated by the display device 123 may also integrate the display of patient identification, treatment instructions and parameters and status from the patient treatment modules 112, 114 into one or more composite images displayed on display devices 123 and 124.

FIG. 2 illustrates an exemplary embodiment of a detail of a patient monitoring/treatment system according to FIG. 1, which includes as monitoring device a patient monitoring module 110 and an imaging module 115 (e.g., x-ray, CT, MRT, etc.), and as patient treatment module a ventilator module 113 or an anesthesia delivery module 114. Those and other elements and features in FIG. 2, which are identical to those shown in FIG. 1 or which perform a similar function, are designated by the same reference number and will not be discussed further. Although the imaging module 115 and the ventilator module 113 are shown in FIG. 2 as being connected to the same PAN, they may be connected to different PANs and communicate via the critical care network 105 and central processor 120, as depicted in FIG. 1.

The central processor 120 may analyze the physiological parameters derived from signals received from the patient monitoring and/or treatment modules 110, 113, 114, 115 to determine if any limits have been exceeded. For example, a physiological parameter response determined by a patient monitoring and/or treatment module may be analyzed and compared to a predetermined parameter range to determine if a limit is exceeded. If a limit has been exceeded, then the central processor 120 may condition output devices on the display devices 123, 124 (FIG. 1) to provide an alarm signal which activates a light, a buzzer, a bell and/or other such device. The central computer 120 may also send a signal over the critical care network 105 and/or the hospital LAN 130 indicating that a limit has been exceeded. A similar alarm may be generated at a remote location in response to the receipt of this signal.

Alternatively or in addition, the central processor 120 may be configured to change parameter values transmitted to the treatment modules 113 and 114 based on physiological parameters derived from the patient monitoring module 110 or imaging module 115, or to adapt, for example, the functionality of the imaging module 115 to the operation of the ventilator module 113, which will now be described.

It is frequently necessary to measure the cardiac output in patients treated with positive pressure ventilation. The algorithm employed for calculating cardiac output from the pulse contour analysis of the arterial blood pressure curve needs to be calibrated with the thermo-dilution method which ideally requires a constant cardiac output. Yet, cardiac output is not constant in patients treated with positive pressure ventilation, because positive pressure ventilation is known to influence the heart and the circulatory system. Due to the increase in intra-thoracic pressure, initially, more blood is filling the left ventricle from the pulmonary circulation, increasing left-ventricular preload and cardiac output into systemic circulation. At the same time, the output of the right ventricle decreases secondary to reduced venous return and reduced right-ventricular preload. Also the output of the left ventricle decreases with the delay corresponding to the time the blood takes to travel through the pulmonary vessels. Consequently, the left ventricular stroke volume varies with positive pressure ventilation, increases during inspiration and decreases during expiration. Hence, the cardiac output changes accordingly.

Increased intrathoracic pressure during measurement of pulmonary arterial pressure (PAP) or pulmonary capillary wedge pressure (PCWP), caused by positive pressure ventilation, is therefore likely to influence the measured pressure which should therefore be measured at the end of expiration.

A patient's spontaneous inspiration could conversely decrease intrathoracic pressure which is why the measurement should ideally take place at end of expiration but prior to the subsequent inspiration.

Likewise, signal quality may be reduced during the acquisition of chest x-rays, CTs or MRTs, if the thorax moves during image acquisition. To improve the quality and accuracy of the measurements, therapeutic devices such as ventilators or anesthesia devices need to be synchronized with patient monitors and diagnostic devices in an intelligent way to avoid potential errors, which may interfere with therapeutic decisions and cause harmful side effects and increase costs.

In general, two different scenarios, which apply to both inspiration and expiration, need to be distinguished:

The elapsed time between the end of a regular, scheduled inspiration and the beginning of a regular, scheduled expiration, or vice versa, is sufficient for the requested imaging or measurement procedure. In this case it is sufficient to delay the acquisition of the image or measurement requested by the operator until the inspiration or expiration is completed. The intrathoracic pressure is then constant during image acquisition or the measurement procedure. If this is done after completed inspiration or expiration depends on the diagnostic objective.

If the elapsed time between a regular scheduled inspiration or expiration is not sufficient, either the end-inspiratory phase or the end-expiratory phase can be extended until a) either the procedure (acquisition of image or measurement) is complete, or b) the situation of the patient is such that immediate gas exchange has priority over signal quality and the extended phase needs to be ended by an immediate inspiration or expiration, respectively. Such abort conditions are, e.g., a violation of the lower threshold for $SpO_2$, reaching a presettable apnoeic time $T_{apn}$, and/or reaching a lower limit value for a minute volume (MV).

Figure 3:
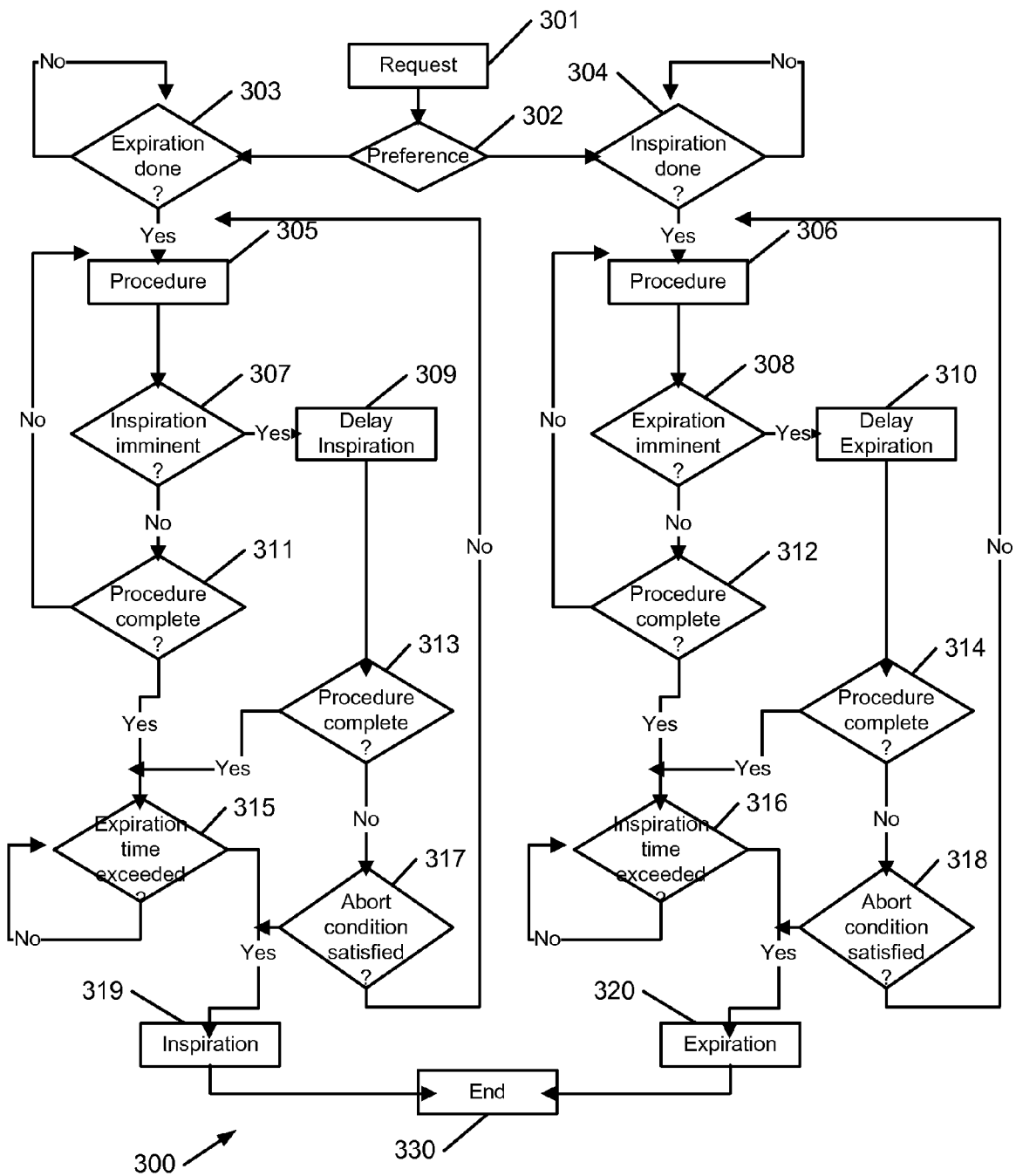
FIG. 3 is a flow diagram for synchronizing operation of a therapeutic device with that of a patient monitoring module.

FIG. 3 shows in form of a process flow diagram 300 synchronization between a therapeutic or treatment module, such as ventilator module 113, and a diagnostic or monitoring module, such as imaging module 115, in a hospital setting with intra-module communication via PAN 116 and/or central processor 120.

In a critical care setting, a patient is connected to a ventilator 113, with a clinician requesting from a central processor 120, at step 301, that a medical imaging or measurement procedure, such as an imaging process with imaging module 115 or determination of Pulmonary Capillary Wedge Pressure (PCWP) with a patient monitoring module 110, be performed. The clinician then selects, at step 302, if the procedure is preferably performed at the end of an expiration cycle or at the end of an inspiration cycle.

If the first scenario is selected, where the procedure is performed after expiration, then it is checked at step 303 if expiration is concluded. The end-of-exhalation time can be detected, for example, by a flow sensor and/or by a pressure measurement. If the expiration has ended, as determined at step 305, then the procedure, such as an image acquisition, is started. The system, e.g., the ventilator module 113, then checks at step 307, if the next ventilation stroke, in this situation inspiration, is imminent and completes the procedure (via steps 311 and 305) if the next inspiration stroke has not yet commenced. If it is determined, at step 311, for example, by a signal received from imaging module 115, that the procedure is complete, then the process 300 goes to step 315 to check if the expiration time has elapsed, in which case the next scheduled inspiration is performed at step 319, and the process 300 terminates at step 330, whereafter the ventilator module resumes its normal operating mode.

Conversely, if it is determined at step 307 that inspiration is imminent although the procedure is still being performed, then the next inspiration is delayed, at step 309, and the status of the procedure is continually checked, at step 313. If it is determined, at step 313, that the procedure has been completed, then the process 300 continues to step 315 as before. However, if it is determined at step 313 that the procedure has not yet been completed, then the process 300 moves to step 317 to check if an abort condition is satisfied. A suitable abort condition may be, for example, a preset apnea time and/or the SpO$_2$ signal from a cooperating patient monitor. When, at step 317, the abort condition is satisfied, the next inspiration begins at step 319, as discussed above.

On the other hand, if the second scenario is selected, where the procedure is performed after inspiration, then it is checked at step 304 if the inspiration is completed. If this is the case, the procedure is started, at step 306. The treatment system, e.g. the ventilator module 113, then checks at step 308, if the next expiration is imminent and completes the procedure (via steps 312 and 306) if the expiration has not yet commenced. If it is determined, at step 312, that the procedure is complete, the process 300 goes to step 316 to check if the inspiration time has elapsed, in which case the next scheduled expiration is performed at step 320, and the process 300 terminates at step 330, whereafter the ventilator module resumes its normal operating mode.

Conversely, if it is determined at step 308 that expiration is imminent although the procedure is still being performed, then the next expiration is delayed, at step 310, and the status of the procedure is continually checked, at step 314. If it is determined, at step 314, that the procedure has been completed, then the process 300 continues to step 316 as before. However, if it is determined at step 314 that the procedure has not yet been completed, then the process 300 moves to step 318 to check if the abort condition is satisfied, as described above. The inspiration time is terminated at step 318 when the abort condition is satisfied, and the next expiration begins at step 320, as discussed above.

If spontaneous respiration is detected at the end of expiration or inspiration, then the spontaneous respiratory activity may render data acquired during that time from a patient monitoring device inaccurate, and the data will be marked as such.

Advantages of automatically coordinating and synchronizing the operation of, for example, a ventilator and an imaging device or a device measuring pulmonary wedge pressure are improved measurement accuracy with greater signal-to-noise ratio, less need for repeated measurements, and more appropriate therapeutic decisions. Advantageously, synchronization leaves the therapy, in this case ventilation, as undisturbed as possible and "schedules" procedures at appropriate points in time, without requiring intervention by the clinician or operator in the decision process. However, to increase accuracy of the data obtained from the patient monitoring devices, the therapy may be modified within the boundaries defined by the patient's measured physiological parameters.

The aforedescribed synchronization between patient monitoring and treatment devices and the automatic adjustment of operating parameters in consonance with established clinical protocols obviate the need for an operator to manually synchronize the operation of different devices to avoid corruption of measurements or image acquisition. Instead, monitoring and treatment modules can be configured for exchange of data, parameters and commands over a hospital network, such as the aforedescribed PAN 116 and critical care network 105, according to predefined rules to assure best diagnostic value while minimizing interruption of or interference with therapy.

The system software may be configured to detect the presence of a module and automatically loads the applications required to control newly added modules 110, 112, 113, 114. Likewise, the system software may be configured to detect when a previously disconnected module is reconnected and resume control of the respective module.

A single configured system as illustrated in FIG. 1 and FIG. 2 can advantageously performs multiple different tests automatically, although manual intervention may be required in some situations. One skilled in the art will understand which patient monitoring and/or treatment modules to include in the system, how to coordinate the operation of these modules, and how to analyze the data from those modules to perform the desired medical tests. A general modular healthcare system has been described in commonly assigned U.S. patent application Ser. Nos. 10/974,982, 10/974,983, 10/976,025, and 11/961,071, the contents of which are incorporated herein by reference in their entirety.

The system reduces human error, improves speed of automatic adaptation of treatment, and aids a clinician in adapting treatment where human intervention is involved. In addition, the system improves the speed and accuracy of generating alerts, which may be crucial in a critical care unit such as an operating room. The system also saves space and cost, combines and groups alarms, provides consolidated documentation, facilitates module transportation and facilitates user operation. It reduces the potential risk in having to control multiple independent monitoring/treatment devices. Because the modules are configured to communicate with each other bidirectionally, tasks of supplying monitoring parameters to therapeutic modules, previously done manually, are advantageously accomplished automatically. The system may employ rules and programmed instruction governing addition of modules to the system. The integrated system advantageously also provides a consistent user interface in both look and feel for the patient monitoring and therapeutic and life sustaining modules. This facilitates user friendly operation and reduces training required to educate a healthcare worker to operate the system compared to individual modules.

While the invention has been disclosed in connection with the preferred embodiments shown and described in detail, various modifications and improvements thereon will become readily apparent to those skilled in the art. Accordingly, the spirit and scope of the present invention is to be limited only by the following claims.

What is claimed is:

1. A method for synchronizing operation between a patient monitoring device and a ventilator, comprising:
    detecting an initial status of the ventilator, the initial status indicating completion of at least one of an inspiration stroke and an expiration stroke;
    starting a procedure performed by the patient monitoring device in response to the initial status of the ventilator;
    monitoring an operating status of at least the patient monitoring device while the procedure is performed;
    while monitoring the operating status of at least the patient monitoring device, detecting an impending event of the ventilator, the impending event to be detected is expiration when the initial status indicates completion of the inspiration stroke, and inspiration when the initial status indicates completion of the expiration stroke;
    while the procedure is performed, delaying at least one of a next inspiration stroke when inspiration is detected to be imminent and a next expiration stroke when expiration is detected to be imminent, wherein the delaying does not exceed a predetermined time; and
    automatically aborting the procedure prior to completion of the procedure and prior to elapsing of the predetermined time when the operating status of at least the patient monitoring device indicates an abort condition, the abort condition being determined in response to a measured patient physiological parameter exceeding a threshold.

2. The method of claim 1, wherein the procedure comprises acquisition of an image with an imaging device.

3. The method of claim 1, wherein the procedure comprises measurement of an intrathoracic blood pressure.

4. The method of claim 3, wherein the intrathoracic blood pressure is a pulmonary arterial pressure (PAP) or a pulmonary capillary wedge pressure (PCWP).

5. The method of claim 1, wherein the abort condition indicates at least one of violating a lower threshold for SpO2, and reaching a lower limit value for a minute volume.

6. A system for synchronizing operation between a patient monitoring device and a ventilator, the system comprising:
    a controller operatively connected to the patient monitoring device and the ventilator, said controller configured to
    detect an initial status of the ventilator, the initial status indicating completion of at least one of an inspiration stroke and an expiration stroke,
    start a procedure performed by the patient monitoring device in response to the initial status of the ventilator,
    monitor an operating status of at least the patient monitoring device while the procedure is performed,
    while the operating status of at least the patient monitoring device is being monitored, detect an impending event of the ventilator, the impending event to be detected is expiration when the initial status indicates completion of the inspiration stroke, and inspiration when the initial status indicates completion of the expiration stroke;
    while the procedure is being performed, delay at least one of a next inspiration stroke when inspiration is detected to be imminent and a next expiration stroke when expiration is detected to be imminent, wherein the delay does not exceed a predetermined time, and
    automatically abort the procedure prior to completion of the procedure and prior to elapsing of the predetermined time, when the operating status of at least the patient monitoring device indicates an abort condition, the abort condition being determined in response to a measured patient physiological parameter exceeding a threshold.

7. The system of claim 6, wherein the patient monitoring device comprises at least one of an imaging device, a pulmonary arterial pressure measuring device, and a pulmonary capillary wedge pressure measuring device.

8. The system of claim 6, wherein the abort condition indicates at least one of a violation of the lower threshold for SpO2, and reaching a lower limit value for a minute volume.

9. The system of claim 6, further comprising:
    an operator console having a display device, said display device configured to display physiological patient data and parameter settings from the patient monitoring device and receiving user input via a graphic user interface (GUI).

10. The method of claim 1, further comprising:
    detecting spontaneous respiration at the end of an expiration stroke or an inspiration stroke; and
    terminating the procedure based on the detection of the spontaneous respiration.

11. The method of claim 10, further comprising:
    marking data acquired from a patient monitoring device during the detected spontaneous respiration as inaccurate.

12. The method of claim 1, further comprising:
    deriving, at the central processor, a new parameter based on signals from at least one of the patient monitoring device and the patient treatment device, the new parameter associated with at least one of a gas exchange, a skin color, a hemodynamics, a pain, and an electro-physiology.

* * * * *